United States Patent [19]

Statton et al.

[11] 4,320,069
[45] Mar. 16, 1982

[54] OXAZOLINE STABILIZED DIPHENYLMETHANE DIISOCYANATE-POLYMETHYLENE POLYPHENYL ISOCYANATE COMPOSITIONS

[75] Inventors: Gary L. Statton, West Chester; John S. Babiec, Jr., Berwyn, both of Pa.

[73] Assignee: Atlantic Richfield Company, Los Angeles, Calif.

[21] Appl. No.: 245,867

[22] Filed: Mar. 20, 1981

[51] Int. Cl.$^3$ .......................................... C07C 119/048
[52] U.S. Cl. ............................ 260/453 SP; 260/453 P
[58] Field of Search ....................... 260/453 SP, 453 P

[56] References Cited

U.S. PATENT DOCUMENTS

| | | | |
|---|---|---|---|
| 3,660,456 | 5/1972 | Naito et al. | 260/453 P |
| 3,962,302 | 6/1976 | Rosenthal et al. | 260/453 P |
| 4,152,348 | 5/1979 | Rabourn | 260/453 SP |
| 4,152,349 | 5/1979 | Rabourn | 260/453 SP |
| 4,162,362 | 7/1979 | Shawl | 560/25 |

Primary Examiner—Dolph H. Torrence
Attorney, Agent, or Firm—Delbert E. McCaslin

[57] ABSTRACT

Liquid reaction product mixtures of diphenylmethane diisocyanates and polymethylene polyphenyl isocyanates resulting from the thermal decomposition of the corresponding carbamates produced by the acid condensation of an N-aryl carbamic acid ester, such as ethylphenylcarbamate, with formaldehyde are storage stabilized against an increase in viscosity and decrease in free NCO content, by incorporating therein an effective amount of a compound having the formula

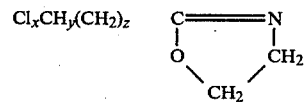

wherein x plus y is equal to 3 and z is an integer of from 0 to 3.

6 Claims, No Drawings

OXAZOLINE STABILIZED DIPHENYLMETHANE DIISOCYANATE-POLYMETHYLENE POLYPHENYL ISOCYANATE COMPOSITIONS

FIELD OF THE INVENTION

The present invention relates to the stabilization of organic isocyanates and more particularly to liquid mixtures of diphenylmethane diisocyanates and the related higher homologs, the polymethylene polyphenyl isocyanates stabilized against degradation and loss of valuable properties with respect to viscosity and free isocyanate groups.

BACKGROUND OF THE INVENTION

Various stablizer compounds have been proposed for incorporation into aromatic polyisocyanate compositions including phenols, phosphites, aryl halides, ureas, thioureas, ureids, acetyls, benzamides, haloacetamides, anilide compounds, tertiary amines and other compounds for color, reactivity and/or storage stability of the isocyanate products, i.e., the diphenylmethane diisocyanates and polymethylene polyphenyl polyisocyanates, prepared by the phosgenation of the corresponding polyamines obtained in the acid condensation of aniline and formaldehyde. Such polyisocyanates produced by phosgenation contain free hydrogen chloride and a wide variety of by-products containing hydrolyzable chloride which affect the overall stability.

U.S. Pat. No. 3,660,456 show, for example, that organic isocyanates prepared by phosgenation may be stabilized by a variety of different compounds and U.S. Pat. Nos. 4,152,348 and 4,152,349 show the use of alkyl oxazolines and oxazines. Many of the isocyanate stabilizer compositions have undesirable properties. Some are highly toxic or have obnoxious odors, while others decrease the effectiveness of catalysts used to prepare polyurethane products from the polyisocyanates.

It is known that diphenylmethane diisocyanates and polymethylene polyphenyl polyisocyanates, devoid of the above noted chloride impurities, also tend to increase in viscosity and decrease in free isocyanate content on storage through reaction of the isocyanate groups to form various polymerics, which process, limits the shelf life of the isocyanates and is undesirable. These diisocyanates and polyisocyanates are prepared by the thermal decomposition of the corresponding carbamates in a suitable solvent as shown, for example, in Rosenthal et al., U.S. Pat. No. 3,962,302; the carbamates having resulted from the acid condensation of N-aryl carbamic acid esters with carbonyl compounds such as formaldehyde as set forth, for example, in Shawl, U.S. Pat. Nos. 4,162,362 and 4,202,986.

SUMMARY OF THE INVENTION

This invention relates to the stabilization of liquid mixtures of diphenylmethane diisocyanates and the higher molecular weight homologs, polymethylene polyphenyl isocyanates, against viscosity increase and free isocyanate loss on storage without undesirable effects on the reactivity of the isocyanate products. More specifically, the present invention concerns the stabilization of a liquid reaction product mixture of diphenylmethane diisocyanates and polymethylene polyphenyl isocyanates prepared by the thermal decomposition of the corresponding diphenylmethane dicarbamates and polymethylene polyphenyl carbamates resulting from the acid catalyzed condensation of an N-aryl carbamic acid ester with formaldehyde.

It is therefore an object of this invention to provide a stabilized liquid mixture of diphenylmethane diisocyanates and polymethylene polyphenyl isocyanates, prepared by the thermal disassociation of the corresponding carbamates, which are substantially free of the abovementioned problems and disadvantages. Another object of this invention is to provide an improved mixture of the liquid diphenylmethane diisocyanates and polymethylene polyphenyl isocyanates which are substantially stable to viscosity changes and loss of free isocyanate (NCO) content.

These and other objects and advantages of this invention will become apparent from the description of the invention which follows and from the claims.

DESCRIPTION OF THE INVENTION

In accordance with the present invention a liquid reaction product mixture of diphenylmethane diisocyanates and polymethylene polyphenyl isocyanates, derived from the thermal decomposition in solvent of the corresponding diphenylmethane dicarbamates and polymethylene polyphenyl carbamates, are stabilized against viscosity changes and loss of free isocyanate (NCO) content by incorporating into the isocyanate in the crude or purified form, from about 0.001 to 1.0 percent preferably from 0.01 to 0.2 percent by weight of a chloroalkyl oxazoline compound having the general formula

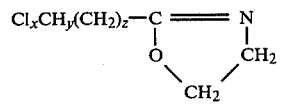

wherein x plus y is equal to 3 and z is an integer of from 0 to 3.

The liquid diphenylmethane diisocyanatepolymethylene polyphenyl isocyanate mixtures which may be stabilized according to the invention are, as indicated hereinabove, prepared by the thermal decomposition of the corresponding carbamates dissolved in a suitable solvent as shown, for example, in U.S. Pat. Nos. 3,962,302 and 3,919,279, with the carbamate being prepared by the acid condensation of an N-aryl carbamic acid ester, such as ethylphenylcarbamate with formaldehyde. Such processes produce liquid diphenylmethane diisocyanatepolymethylene polyphenyl isocyanate mixtures containing from about 20 to 85 weight percent diphenylmethane diisocyanate as the 4,4' and 2,4' isomers with a minor amount of the 2,2' isomer, with the balance of the mixture being the related higher molecular weight polymethylene polyphenyl isocyanates and from about 3 to 9 percent by-product impurities such as carbodiimides, biurets and ureas which result from the condensation and decomposition reactions. Of the diphenylmethane dicarbamates in the carbamate product mixture, the 4,4' isomer to 2,4' isomer will range from about 4:1 to 20:1 as is described for example in U.S. Pat. No. 4,230,877.

The stabilizer compounds having the formula hereinabove described which may be employed with the liquid diphenylmethane diisocyanate-polymethylene polyphenyl isocyanate mixtures include, for example, chloromethyl oxazoline, chloroethyl oxazoline, chloropropyl oxazoline, chlorobutyl oxazoline, dichloromethyl, ethyl, propyl or butyl oxazoline and trichloromethyl, ethyl, propyl or butyl oxazoline. The stabilizing compounds are simply mixed with the liquid diphenylmethane diisocyanatepolymethylene polyphenyl isocyanate mixture at any reasonable temperature preferably ambient temperatures. Standard handling procedure for the polymeric isocyanates after addition of the stabilizer compound is adequate. The amount of stabilizer employed should be adjusted to provide adequate stabilization against the undesired degradation effects on storage and its preferably in the range of from about 0.01 to about 0.20 percent by weight based on the weight of the liquid isocyanate mixture.

2-oxazoline stabilized sample had a viscosity of 254 cp. at 25° C. and an NCO content of 30.3.

EXAMPLE 2 to 9

In Examples 2 to 9, which follow in Table form the procedure of Example 1 was repeated employing various stabilizers, amount of stabilizer and conditions with 25 cc. sample bottles of the same 30.7 NCO and 178 cp. viscosity liquid diphenylmethane diisocyanate-polymethylene polyphenyl isocyanate mixture of Example 1. Analysis for the NCO content and viscosity of the solutions, including control samples, showing the effect of the stabilizers are set forth.

TABLE

| Example No. | Stabilizer (% by Wt.) | Temp. °C. | Time (hrs.) | NCO % | Viscosity (cp. at 25° C.) |
|---|---|---|---|---|---|
| 2 | dichloromethyl oxazoline (0.043) | 62 | 476 | 30.1 | 253 |
| — | Example 2 Control | 62 | 476 | 28.8 | 1470 |
| 3 | chloroethyl oxazoline (0.10) | 30 | 720 | 30.2 | 240 |
| — | Example 3 Control | 30 | 720 | 28.9 | 1481 |
| 4 | chlorobutyl oxazoline (0.20) | 50 | 720 | 30.3 | 220 |
| — | Example 4 Control | 50 | 720 | 28.7 | 1560 |
| 5 | dichloroethyl oxazoline (0.40) | 30 | 1440 | 30.4 | 185 |
| 6 | dichloropropyl oxazoline (0.25) | 30 | 1440 | 30.3 | 210 |
| — | Example 5, 6 Control | 30 | 1440 | 28.9 | 1610 |
| 7 | trichloromethyl oxazoline (0.075) | 62 | 476 | 30.5 | 230 |
| — | Example 7 Control | 62 | 476 | 28.6 | 1475 |
| 8 | trichlorobutyl oxazoline (0.30) | 50 | 720 | 30.6 | 180 |
| — | Example 8 Control | 50 | 720 | 28.6 | 1520 |
| 9 | dichloromethyl oxazoline (.015) | 30 | 720 | 30.2 | 240 |
| — | Example 9 Control | 30 | 720 | 28.9 | 1510 |

The stabilized isocyanates of the instant invention are valuable starting materials for the preparation of polyurethanes and for use in reactions and other applications conventional in the art for such liquid diphenylmethane diisocyanate-polymethylene polyphenyl isocyanate mixtures. The stabilizers of the instant invention do not in any way detract from the reactivity or other behaviour of the isocyanates.

The following examples are provided to illustrate the invention in accordance with the principles of this invention, but are not to be construed as limiting the invention in any way except as indicated by the appended claims.

EXAMPLE 1

0.068 percent by weight 2-chloro-2-oxazoline was added as stabilizer to a liquid mixture of diphenylmethane diisocyanates and the higher molecular weight homologs polymethylene polyphenyl isocyanates, (prepared by the condensation of ethylphenylcarbamate with formaldehyde as set forth in U.S. Pat. No. 4,162,362 followed by thermal decomposition of the carbamate to the isocyanate per U.S. Pat. No. 3,962,302). The isocyanate mixture containing the oxazoline stabilizer was placed in a 25 cc bottle which was purged with nitrogen, capped and sealed along with a 25 cc control sample bottle of unstabilized isocyanate. The initial isocyanate (NCO) content of the samples was 30.7 with a viscosity of 178 centipoise (cp.) at 25° C. The bottles were placed in an oven at 62° C. for 476 hours after which the samples were removed and analyzed for viscosity and NCO content. The control sample showed a viscosity of 1470 cp. at 25° C. with an NCO content of 28.8 percent while the 2-chloromethyl-

We claim:

1. A method for the storage stabilization of liquid diphenylmethane diisocyanate-polymethylene polyphenyl isocyanate mixtures derived from the thermal decomposition of the corresponding diphenylmethane dicarbamates and polymethylene polyphenyl carbamates prepared by the acid condensation of N-aryl carbamic acid ester with formaldehyde, which comprises incorporating in said liquid isocyanate mixture from about 0.001 to 1.0 percent by weight of a chloroalkyl oxazoline compound having the formula

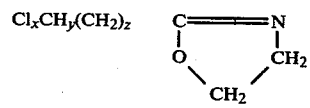

wherein x plus y is equal to 3 and z is an integer of from 0 to 3.

2. A method according to claim 1 wherein the oxazoline compound is selected from the group consisting of chloromethyl oxazoline, dichloromethyl oxazoline, chloroethyl oxazoline, chlorobutyl oxazoline, dichloroethyl oxazoline, dichloropropyl oxazoline, trichloromethyl oxazoline and trichlorobutyl oxazoline.

3. A method according to claim 2 wherein the chloroalkyl oxazoline is chloromethyl oxazoline.

4. A method according to claim 2 wherein the chloroalkyl oxazoline is dichloromethyl oxazoline.

5. A method according to claim 1 wherein the chloroalkyl oxazoline compound is employed in an amount of from 0.01 to 0.2 percent by weight.

6. A process according to claim 1 wherein the diphenylmethane diisocyanate content of the liquid isocyanate mixture is from about 20 to 85 weight percent.

* * * * *